United States Patent
Elliott et al.

(10) Patent No.: US 6,399,590 B2
(45) Date of Patent: *Jun. 4, 2002

(54) PHOSPHOGLYCOLIPID AND METHODS FOR ITS USE

(75) Inventors: Gary T. Elliott, Stevensville; Patricia A. Weber; C. Gregory Sowell, both of Hamilton, all of MT (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/927,246

(22) Filed: Aug. 10, 2001

Related U.S. Application Data

(63) Continuation of application No. 09/429,238, filed on Oct. 28, 1999, now abandoned, which is a continuation of application No. 09/138,305, filed on Aug. 21, 1998, now Pat. No. 6,013,640.

(51) Int. Cl.$^7$ .......................... A61K 31/715; C08B 37/00
(52) U.S. Cl. .............................. 514/53; 536/53; 536/55; 536/55.1; 536/123.13
(58) Field of Search .............................. 514/53; 536/53, 536/55, 55.1, 123.13

(56) References Cited

U.S. PATENT DOCUMENTS

| 4,436,727 A | 3/1984 | Ribi |
| 4,912,094 A | 3/1990 | Myers et al. |
| 5,286,718 A | 2/1994 | Elliot |

FOREIGN PATENT DOCUMENTS

| DE | 3921416 A1 | 1/1990 |
| WO | 99/20284 A1 | 4/1999 |

OTHER PUBLICATIONS

Baker, et al. "Structural Features that Influence the Ability of Lipid A and its Analogs to Abolish Expression of Suppressor T Cell Activity" *Infection and Immunity* (Jul. 1992), vol. 60(7), pp. 2694–2701.

Bensard, et al. "Induction of Endogenous Tissue Antioxidant Enzyme Activity Attenuates Myocardial Reperfusion Injury" *J. of Surgical Resesarch* (1990), vol. 49, pp. 126–131.

Berg, et al. "Endotoxin Extends Survival of Adult Mice in Hyperoxia" *Proc Soc Exp Biolo Med* (1990), vol. 193, pp. 167–170.

Brown, et al. "Endotoxin Pretreatment Increases Endogenous Myocardial Catalase Activity and Decreases Ischemia–reperfusion Injury of Isolated Rat Hearts", *Proc Nat Acad Sci*, 1989, vol. 86, pp. 2516–2520.

Elliot, Gary T., "Monophosphoryl Lipid A Induces Delayed Preconditioning Against Cardiac Ischemia–Reperfusion Injury" *J. Mol Cell Cardiol* (1998), vol. 30, pp. 3–17.

Flynn, et al. "A Sialyl Lewis–containing Carbohydrate Reduces Infarct Size: Role of Selectins in Myocardial Reperfusion Injury" *Am. J. Physiology*, 1996, vol. 271(5), pp. 2086–2096.

Kuhn, et al. "Characterization of the Epitope Specificity of Murin Monoclonal Antibodies Directed Against Lipid A" *Infection and Immunity*, (Jun. 1992) vol. 60(6), pp. 2201–2210.

Maulik, et al. "Myocardial Adaptation to Ischemia by Oxidative Stress Induced by Endotoxin" *Am. J. Physiology*, 1995, vol. 269, pp. c907–c916.

Mizumura, et al. "Bimakalim, an ATP–sensitive Potassium Channel Opener, Mimics the Effects of Ischemic Preconditioning to Reduce Infarct Size . . . " *Ciruclation* (1995), vol. 92, pp. 1236–1245.

*Primary Examiner*—Kathleen K. Fonda
(74) *Attorney, Agent, or Firm*—Townsend and Townsend and Crew LLP

(57) ABSTRACT

The invention concerns a novel phosphoglycolipid compound. The compound of the subject invention is 2-Deoxy-6-O-[2-deoxy-4-O-phosphono-3-O-[(R)-3-tetradecanoyloxytetradecanoyl]-2-[(R)-3-octadecanoyloxytetradecanoylamino]-β-D-glucopyranosyl]-2-[(R)-3-hexadecanoyloxytetradecanoylamino]-D-glucopyranose and pharmaceutically acceptable salts thereof. The compound is not immunoreactive, not pyrogenic, not toxic but is active in ameliorating tissue damage due to ischemia/reperfusion injury. Methods for using the subject compound to protect against reversible and irreversible damage due to ischemia/reperfusion injury are also disclosed.

17 Claims, 6 Drawing Sheets

PHOSPHOGLYCOLIPID AND METHODS FOR ITS USE

CROSS-REFERENCE TO RELATED APPLICATIONS

This application is a continuation of and claims the benefit of U.S. application Ser. No. 09/429,238, filed Oct. 28, 1999, now abandoned, which is a continuation of Ser. No. 09/138,305, filed Aug. 21, 1998, now U.S. Pat. No. 6,013,640, the disclosures of which are incorporated herein by reference, in their entirety for all purposes.

BACKGROUND OF THE INVENTION

Damage caused to tissues during ischemia/reperfusion can be extensive. Tissues deprived of oxygen suffer both reversible and irreversible damage. Injured tissues can also display disorders in automaticity. For example, myocardial tissues damaged during ischemia/reperfusion can display irreversible damage or myocardial infarction. Reversible damage, or stunning, is apparent with reduced pump efficiency leading to decreased cardiac output and symptomatology of suboptimal organ perfusion. Reperfusion of ischemic myocardial tissue may also cause electrophysiologic changes causing disorders in automaticity, including lethal arrythmias.

The exact mechanisms by which tissues are damaged during ischemia/reperfusion are unknown. It is hypothesized, however, that a complex series of events occur where tissues are damaged during ischemia as well as during subsequent reperfusion. During ischemia, tissues are deprived of oxygen-giving blood leading to anaerobic metabolism and consequently intracellular acidosis. Lack of circulation can cause infarcts or areas of necrotic, dead tissue. Ischemic tissues produce less of the enzymes needed to scavenge free radicals. Upon reperfusion and re-exposure to oxygen, tissues are damaged when free radicals including hydroxyl radicals are produced. Oxidative damage also disrupts the calcium balance in surrounding tissues causing stunning. Damage due to the oxidative burst is further compounded when injured cells release factors which draw inflammatory neutrophils to the ischemic site. The inflammatory cells produce enzymes which produce more toxic free-radicals and infiltrate the interstital spaces where they kill myocytes.

Methods to protect against the damage due to ischemia/reperfusion injury focus on reducing the initial oxidative burst and ensuing calcium overload preventing subsequent inflammation-associated damage. For example, agents which either decrease the production of oxygen-derived free radicals (including allopurinol and deferroxamine) or increase the catabolism of these materials such as superoxide dismutase, catalase, glutathione, and copper complexes, appear to limit infarct size and also may enhance recovery of left ventricular function from cardiac stunning. Agents which block sarcolemmal sodium/hydrogen exchange such as amiloride prevent the obligatory influx of calcium into the cell attendant with sodium extrusion and consequently reduce calcium overload.

Tissues can also be protected from ischemia/reperfusion injury by ischemic preconditioning. Ischemic preconditioning is triggered by brief antecedent ischemia followed by reperfusion which results in the rapid development of ischemic tolerance. This acute preconditioned state of ischemic tolerance lasts 30 min to 2 h and in myocardial tissue is characterized by reduced infarct size and a reduced incidence of ventricular arrythmias but not reduced levels of stunning (Elliot, 1998). Following dissipation of the acute preconditioned state, even in the absence of additional periods of preconditioning ischemia, a delayed preconditioned state of ischemic tolerance appears 12–24 h later and lasts up to 72 h. During the delayed phase of preconditioning protection against myocardial infarction, stunning and arrhythmia have been reported in various species.

Features of preconditioned myocardium in the face of ischemia/reperfusion include preservation of adenosine triphosphate (ATP) in some models, attenuation of intracellular acidosis and the reduction of intramyocyte calcium loading. Certain chemical agents known to be released by myocardium during ischemia have been shown to induce acute and delayed ischemic tolerance and provide cardiac protection. For example, adenosine, bradykinin and opiate receptor agonists which induce acute preconditioning appear to protect from ischemic injury via ATP dependent potassium (KAT) channel signaling pathways. The agent, bimakalim, known to open the KATP channel has also been shown to limit infarct size (Mizumura et al., 1995). Monophosphoryl lipid A (MLA) prevents irreversible as well as reversible damage to ischemic tissues (Elliot U.S. Pat. No. 5,286,718). Monophosphoryl lipid A is a detoxified derivative of lipid A, the active substructural element of lipopolysaccharide (LPS). LPS or endotoxin is a potent immunomodulator produced by most strains of Gram-negative bacteria. Pretreatment with LPS prior to ischemia has been shown to increase myocardial catalase activity increasing myocardial function (Brown et al., Bensard et al.). Endotoxin also protects against lung injury during hypoxia (Berg et al.). The cardioprotective effect of high doses of endotoxin appears to be associated with the ability of this "toxin" to induce upon pretreatment myocardial oxidative stress, thereby protecting from a second oxidative stress associated with ischemia (Maulik et al.). LPS however is quite toxic. MLA has been structurally modified to negate the toxicity of LPS. It is hypothesized that MLA protects against injury due to ischemia/reperfusion injury by inducing the production of nitric oxide synthase which leads to an enhanced open-state probability of the cardioprotective ATP-dependent potassium channel (KATP). The nitric oxide burst caused by MLA may also lead to a decrease in the number of inflammatory neutrophils entering the post-ischemic area protecting the patient from further injury. In contrast to endotoxin, MLA does not appear to induce myocardial oxidative stress at cardioprotective doses.

Current treatments for ischemia/reperfusion injury are not however without drawbacks. Many of the agents known to be active, do not have broad clinical applicability, have limited effectiveness, and/or have dose limiting toxicities and consequently have been restricted in their application to ameliorate ischemia/reperfusion injury in the heart. Endotoxin is highly toxic to the system at cardioprotective doses. MLA, while non-toxic, is manufactured by the fermentation of *S. minnesota* and, as is the case with many biological products, exists as a composite or mixture of a number of molecular congeners varying in fatty acid substitution patterns with varying fatty acid chain lengths.

Although in comparison with endotoxin, MLA is non-toxic at cardioprotective doses, MLA can cause mild, transient, although not dose-limiting, fever in the target dose range. It should therefore be apparent from the above that a need remains for new compositions which are safe, effective and which have a broad clinical applicability in preventing or ameliorating the harmful effects of ischemia/reperfusion. Compositions which are non-toxic, non-pyrogenic, produced by chemical synthesis and of a single defined molecular structure would prove advantageous for this application.

SUMMARY OF THE INVENTION

The subject invention concerns a novel phosphoglycolipid useful in ameliorating the damage due to ischemia/reperfusion injury. Specifically, the claimed phosphoglycolipid is 2-Deoxy-6-O-[2-deoxy-4-O-phosphono-3-O-[(R)-3-tetradecanoyloxytetradecanoyl]-2-[(R)3-octadecanoyloxytetradecanoylamino]-β-D-glucopyranosyl]-2-[(R)-3-hexadecanoyloxytetradecanoylamino]-D-glucopyranose and has the following structure:

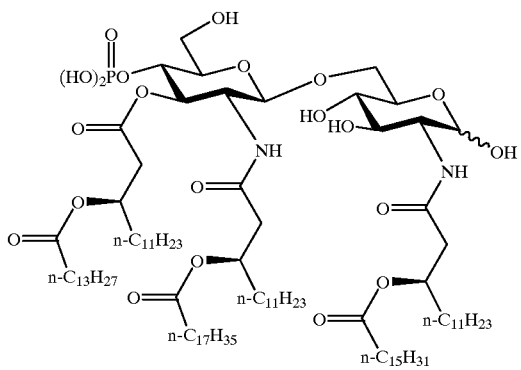

The phosphoglycolipid compound of the subject invention can be chemically synthesized using protocols described in the subject application.

Methods for using this novel phosphoglycolipid to ameliorate the damage due to ischemia/reperfusion injury are also described. The compound of the subject invention is particularly advantageous for this application because it does not induce fever or proinflammatory cytokines at dose levels anywhere near the cardioprotective dose range which may substantially increase the maximum tolerated dose and therefore the likelihood of achieving a therapeutic dose level in humans especially when administered immediately prior to surgery.

DETAILED DESCRIPTION OF THE SUBJECT INVENTION

Figure 1:
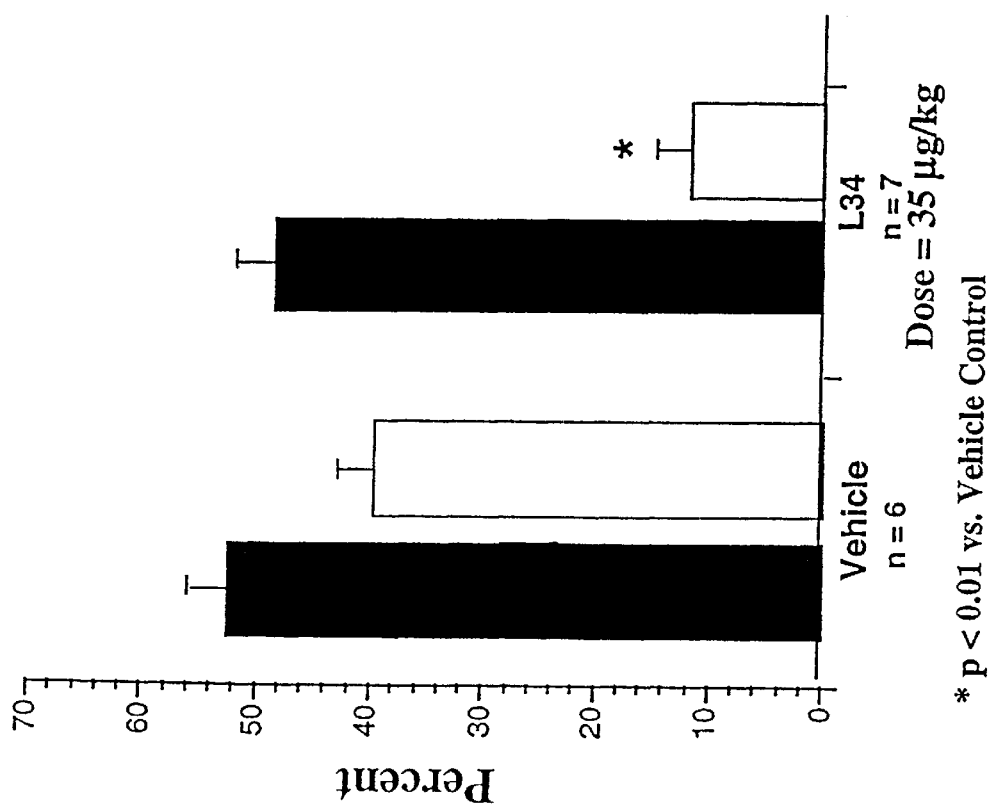
FIG. 1 shows the cardioprotective effect of the compound of the subject invention (35 μg/kg) against infarction given 24 h before ischemia in a rabbit model of regional myocardial ischemia. ■ % Left Ventricle at Risk; □ % Infarct in Risk Area; * p<0.01 vs. Vehicle Control.

The subject invention concerns a novel phosphoglycolipid, specifically, a 2-Deoxy-6-O-[2-deoxy-4-O-phosphono-3-O-[(R)-3-tetradecanoyloxytetradecanoyl]-2-[(R)-3-octadecanoyloxytetradecanoylamino]-β-D-glucopyranosyl]-2-[(R)-3-hexadecanoyloxytetradecanoylamino]-D-glucopyranose and pharmaceutically acceptable salts thereof. The compound of the subject invention has the following structure:

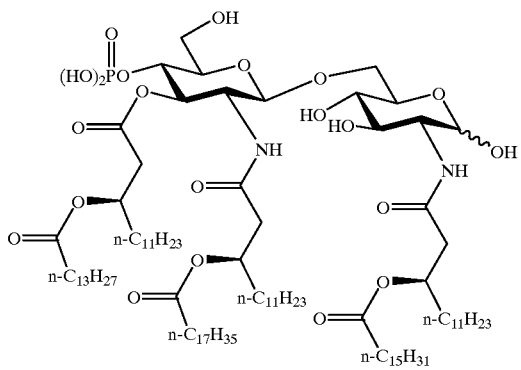

The phosphoglycolipid compound of the subject invention is useful in ameliorating tissue damage due to ischemia/reperfusion injury.

The compound of the subject invention, hereinafter referred to as L34, can be synthesized by coupling an N-acyloxyacylated or N-protected glycosyl acceptor unit with a suitably protected and/or 3-O-acyloxyacylated glycosyl donor unit via a Koenigs-Knorr type reaction. In a preferred embodiment, the compound of the subject invention (compound 1) is constructed from the known starting materials benzyl 2-amino-2-deoxy-4,6-O-isopropylidene-β-D-glucopyranoside (compound 2) and 2-(trimethylsilyl)ethyl 2-amino-2-deoxy-4,6-O-isopropylidene-β-D-glucopyranoside (compound 5) as shown in Scheme 1

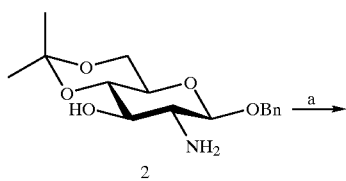

2

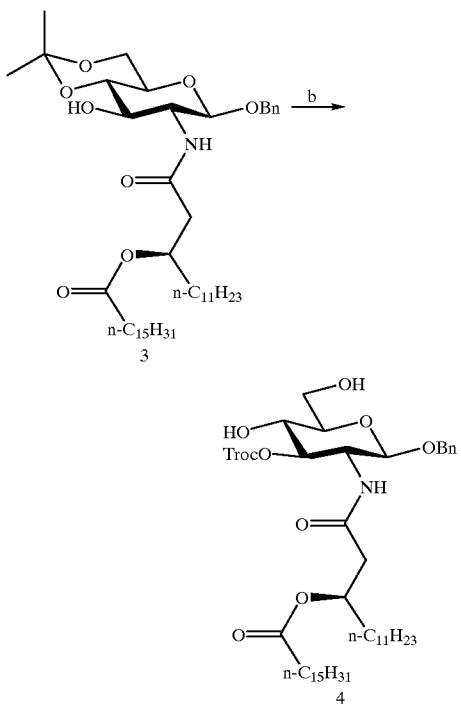

(a)(R)-3-hexadecanoyloxytetradecanoic acid, EDC•MeI, CH$_2$Cl$_2$; (b)Troc-Cl, DMAP, pyridine, CH$_2$Cl$_2$; then 80% aq. AcOH, 60° C.

Scheme 2

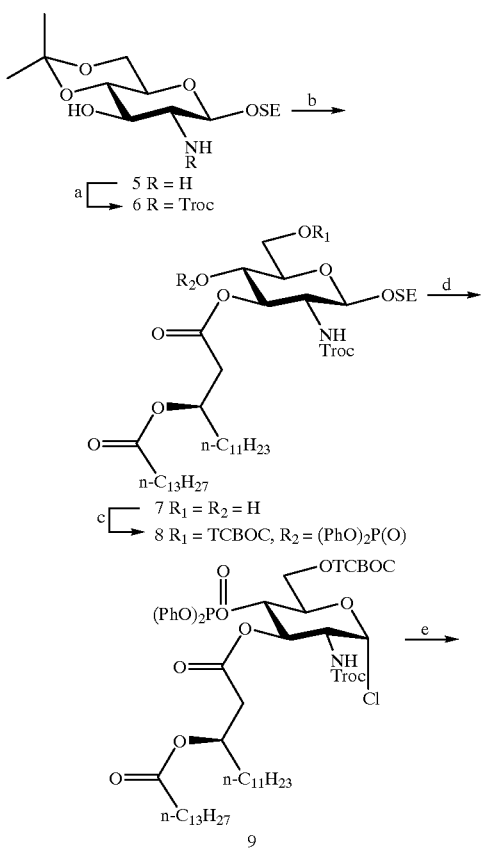

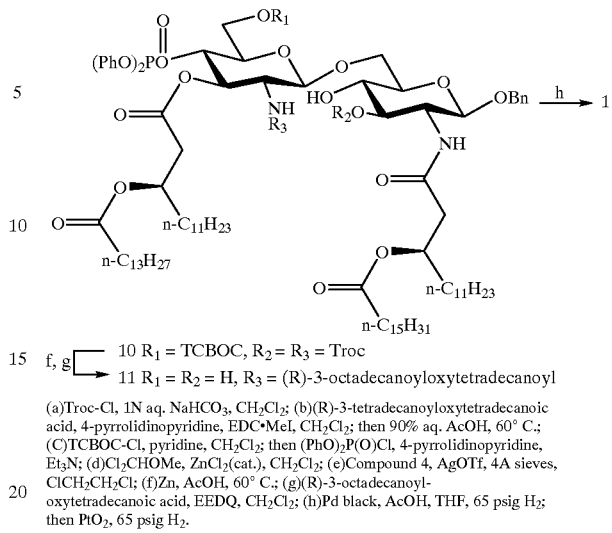

(a)Troc-Cl, 1N aq. NaHCO$_3$, CH$_2$Cl$_2$; (b)(R)-3-tetradecanoyloxytetradecanoic acid, 4-pyrrolidinopyridine, EDC•MeI, CH$_2$Cl$_2$; then 90% aq. AcOH, 60° C.; (C)TCBOC-Cl, pyridine, CH$_2$Cl$_2$; then (PhO)$_2$P(O)Cl, 4-pyrrolidinopyridine, Et$_3$N; (d)Cl$_2$CHOMe, ZnCl$_2$(cat.), CH$_2$Cl$_2$; (e)Compound 4, AgOTf, 4A sieves, ClCH$_2$CH$_2$Cl; (f)Zn, AcOH, 60° C.; (g)(R)-3-octadecanoyl-oxytetradecanoic acid, EEDQ, CH$_2$Cl$_2$; (h)Pd black, AcOH, THF, 65 psig H$_2$; then PtO$_2$, 65 psig H$_2$.

Schemes 1 and 2. N-acylation of compound 2 with (R)-3-hexadecanoyloxytetradecanoic acid in the presence of 1-(3-dimethylaminopropyl)-3-ethylcarbodiimide methiodide (EDC.MeI) gives intermediate 3. Hydroxyl protection with 2,2,2-trichloroethyl chloroformate (Troc-Cl) and acetonide hydrolysis then provides glycosyl acceptor 4.

For the synthesis of glycosyl donor 9, N-protection of compound 5 under Schotten-Baumann conditions with Troc-Cl affords compound 6. 3-O-Acylation with (R)-3-tetradecanoyloxytetradecanoic acid in the presence of EDC.MeI and 4-pyrrolidinopyridine followed by acetonide cleavage gives diol 7 which is then converted to compound 8 by treatment with 1,1-dimethyl-2,2,2-trichloroethyl chloroformate (TCBOC-Cl) and diphenyl chlorophosphate. Transformation of compound 8 into glycosyl donor 9 is then accomplished with α,α-dichloromethyl methyl ether in the presence of zinc chloride or by other methods known in the art.

Coupling of compounds 4 and 9 is achieved by a Koenigs-Knorr-type reaction in the presence of silver triflate or other suitable catalyst to give disaccharide 10. The trichloroethyl-based protecting groups are then removed with zinc dust in acetic acid and the glucosamine nitrogen is selectively acylated with (R)-3-octadecanoyloxytetradecanoic acid in the presence of a suitable coupling reagent such as 2-ethoxy-1-ethoxycarbonyl-1,2-dihydroquinoline (EEDQ) to give the hexaacylated derivative 11. The remaining protecting groups of compound 11 are then cleaved by catalytic hydrogenation in the presence of palladium and platinum catalysts to give compound 1.

One skilled in the art would realize that the introduction of the phosphate and (R)-3-n-alkanoyloxytetradecanoyl groups into the glucosamine units does not necessarily have to be performed in the order shown in Schemes 1 and 2, or described in Example 1 below. Installation of these groups also can be performed subsequent to the glycosylation (coupling) reaction using N- and O-protecting groups suitable for the chemical differentiation of the amino and hydroxyl groups present. Also, protecting groups other than those shown in Schemes 1 and 2 or described in Example 1 below can be employed for temporary protection of the phosphate, hydroxyl, and amino groups during the synthesis. Typical protecting groups for the phosphate group include, but are not limited to, phenyl, benzyl, and o-xylyl; preferably, the phosphate group is protected with two phenyl groups. The 6-position can be temporarily protected by blocking groups commonly used in sugar chemistry such as silyl, benzyl, or benzyloxymethyl ethers or an alkyl carbonate; preferably, the 6-hydroxyl group is protected as a 1,1-dimethyl-2,2,2-trichloroethyl carbonate (TCBOC). N-Protecting groups for the sugar amino groups include, but are not limited to, commonly employed carbamates such as t-butyl (t-BOC), benzyl (Cbz), 2,2,2-trichloroethyl (Troc), and 9-fluorenylmethyl (Fmoc); preferably, the amino group of the glycosyl donor (e.g., compound 9) is protected with a Troc group. Additionally, other activating or leaving groups attached to the anomeric center of the glycosyl donor besides chloride can be used in the coupling reaction. Commonly used activating groups include, but are not limited to, fluoride, chloride, bromide, acetoxy, and trichloroacetimidate.

The compound of the subject invention can be in the form of any pharmaceutically acceptable salt. Salts of the compound useful according to the subject invention include triethylamine, triethanolamine, tris, glycine and ammonium salts. One skilled in the art would recognize other suitable salts included in the subject invention.

The novel phosphoglycolipid of the subject invention is useful in ameliorating damage to metabolically active tissues such as, but not restricted to, heart tissue due to ischemia/reperfusion injury. Tissues are initially damaged during ischemia when they are deprived of oxygen. Oxygen deprivation during ischemia causes cell necrosis. Oxygen deprivation also leads to increased free-radical production upon reperfusion, activation of the complement pathway, upregulation of vascular adhesion molecules and the production of inflammatory cytokines. The compound of the subject invention protects tissues deprived of oxygen during ischemia. It should be apparent to those skilled in the art that the subject compound should also protect tissues experiencing all types of hypoxia or anoxia followed by reoxygenation.

It has been suggested that additional damage and cell death occurs upon the reintroduction of oxygen to the tissues by reperfusion. Free-radicals produced during reperfusion promote cell death. Free-radical damage to cells results in calcium overload and a decrease in activity of a variety of enzyme systems including, presumably, nitric oxide synthase causing a decrease in nitric oxide production leading to increases in neutrophil adhesion. The cardioprotective effect of the compound of the subject invention can be blocked by aminoguanidine, a selective inhibitor of inducible nitric oxide synthase (iNOS). Administration of the drug blocked the delayed cardioprotective effect of L34 in dogs suggesting a nitric oxide-linked mechanism of action for the subject compound.

Neutrophils are instrumental in the damaging inflammatory response which occurs in post-ischemic tissues. Neutrophils are called to the ischemic site by C5a and 5b (complement fragments), cytokines and chemokines which are chemotactic for the cell. Activated neutrophils attach to endothelial cells and diapedes across the endothelial barrier where they kill myocytes. Attachment and diapedesis of inflammatory neutrophils across the endothelial barrier are dependent upon the upregulation of adhesion molecules on both the endothelial surface and the neutrophil. Cytokines such as IL-6 produced by ischemic tissues have been shown to be crucial to the upregulation of adhesion molecules. The compound of the subject invention is unique in that at protective levels it does not induce pro-inflammatory cytokines or fever yet is effective in ameliorating damage due to ischemia/reperfusion injury. It is understood that closely related compounds possessing fatty acid residues of similar chain lengths would be expected to display like biological activities.

In the clinical situation, ischemic events occur which are anticipated or unexpected. Planned surgeries causing ischemic events include coronary artery bypass surgery, heart valve replacement, cardiac angioplasty, ventricular septal repairs, surgery with major vessel cross-clamping, plastic surgery, skin flap translocation, myoplasty, organ or tissue transplant, aortic aneurysm repair or bowel resection. Tissues can be deprived of oxygen during unplanned events such as myocardial infarction, stroke, drowning, bowel infarct and traumatic amputation and reattachment. Unexpectedly, the phosphoglycolipid compound of the subject invention provides both acute protection as well as delayed protection to ischemic tissues. Further, duration of the acute protective effect can be extended by infusion of the drug following a bolus dose.

The compound of the subject invention provides a protective effect to ischemic tissues within minutes of administration of the compound to a patient. For example, administration of the compound of the subject invention to test animals 10 min before cardiac ischemia induced protection shown by reduced infarct size and stunning in treated animals. This immediate or acute protective effect dissipates or wanes in time. A delayed protective effect however becomes apparent approximately 24 h after administration of the drug. Delayed protection was evident in dogs and rabbits when animals were treated with the compound of the subject invention 24 h before cardiac ischemia as illustrated by reduced infarct size and stunning. Protection provided by the compound of the subject invention to ischemic tissues is biphasic offering two distinct periods of protection, an acute period of protection and a delayed period of protection. It has been found that the acute protective effect of L34 can be extended for at least 3 h by infusion of the drug immediately following bolus dosing allowing a clinician to bridge the gap between acute and delayed periods of protection. The compound of the subject invention is advantageous in that it can be used successfully in emergency and trauma situations where it is not possible to dose well in advance of an oxygen depriving event. Further, the delayed protective effect provided by the compound makes the drug useful in situations where the ischemic events may occur even a day following administration of a single dose.

In methods for protecting against ischemic damage, the compound of the subject invention can be formulated with a pharmaceutically acceptable carrier for injection, inhalation or intranasal, rectal or vaginal instillation or ingestion. As used herein, "pharmaceutically acceptable carrier" means a medium which does not interfere with the biological activity of the active ingredient and is not toxic to the patient to whom it is administered. Pharmaceutically acceptable carriers include oil-in-water or water-in-oil emulsions, aqueous compositions with or without inclusion of organic co-solvents suitable for intravenous (IV) use, liposomes or surfactant containing vesicles, microbeads and microsomes, powders, tablets, capsules, suppositories or aqueous suspensions and aerosols.

Formulations of the compound of the subject invention that can be administered parenterally, i.e. intraperitoneally, subcutaneously, intramuscularly or intravenously include the following preferred carriers. An example of a preferred carrier for intravenous use includes a mixture of 10% USP ethanol, 40% USP propylene glycol or polyethylene glycol 600 and the balance USP Water for Injection (WFI). Other acceptable carriers include 10% USP ethanol and USP WFI;

0.01–0.1% triethanolamine in USP WFI; or 0.01–0.1% dipalmitoyl diphosphatidylcholine; and 1–10% squalene or parenteral vegetable oil-in-water emulsion. Pharmaceutically acceptable parenteral solvents are such as to provide a solution or dispersion which may be filtered through a 0.22 micron filter without removing the active ingredient.

Examples of preferred carriers for subcutaneous or intramuscular use include phosphate buffered saline (PBS) solution, 5% dextrose in WFI and 0.01–0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride and 1 to 10% squalene or parenteral vegetable oil-in-water emulsions.

Examples of carriers for administration via mucosal surfaces depend upon the particular route. When administered orally, examples include pharmaceutical grades of mannitol, starch, lactose, magnesium stearate, sodium saccharide, cellulose, magnesium carbonate and the like, with mannitol being preferred. When administered intranasally, polyethylene glycol, phospholipids, glycols and glycolipids, sucrose, and/or methylcellulose, powder suspensions with or without bulling agents such as lactose and preservatives such as benzalkonium chloride, EDTA, may be used. In a particularly preferred embodiment, the phospholipid 1,2 dipalmitoyl-sn-glycero-3-phosphocholine (DPPC) is a suitable isotonic aqueous carrier at 0.01–0.1% for intranasal administration of the compound of the subject invention at a concentration of 0.1 to 3.0 mg/ml. When administered by inhalation, suitable carriers are polyethylene glycol or glycols, DPPC, methylcellulose, dispensing agents, and preservatives, with polyethylene glycols and DPPC being preferred.

The compound of the subject invention is administered to an individual in "an effective amount" to ameliorate or protect from ischemia/reperfusion injury. As used herein, "an effective amount" is that amount which shows a response over and above the vehicle or negative controls. The precise dosage of the compound of the subject invention to be administered to a patient will depend the route of administration, the pharmaceutical composition, and the patient. For example, when administered intravenously, to pigs to reduce infarct size after left anterior descending artery occlusion, the amount of compound used is from 1 to about 1000 micrograms/kg, preferably from about 10 to about 300 micrograms/kg, and most preferably from about 35 to about 100 micrograms per kilogram of body weight.

Following are examples which illustrate procedures for practicing the invention. All percentages are by weight and all solvent mixture proportions are by volume unless otherwise noted.

EXAMPLE 1

Preparation of the Novel Phosphoglycolipid (L34)

Preparation of 2-Deoxy-6-O-[2-deoxy-4-O-phosphono-3-O-[(R)-3-tetradecanoyloxytetradecanoyl]-2-[(R)-3-octadecanoyloxytetradecanoylamino]-β-D-glucopyranosyl]-2-[(R)-3-hexadecanoyloxytetradecanoylamino]-D-glucopyranose Triethylammonium Salt (Compound 1)

(1) A solution of benzyl 2-amino-2-deoxy-4,6-O-isopropylidene-β-D-glucopyranoside (compound 2, 0.432 g, 1.40 mmol) and (R)-3-hexadecanoyloxytetradecanoic acid (0.70 g, 1.54 mmol) in $CH_2Cl_2$ was treated with EDC.MeI (0.62 g, 2.10 mmol) and stirred for 16 h at room temperature. The reaction mixture was concentrated and the resulting residue purified by flash chromatography on silica gel (gradient elution, 35–45% EtOAc-hexanes) to give 0.89 g (85%) of benzyl 2-deoxy4,6-O-isopropylidene-2-[(R)-3-hexadecanoyloxytetradecanoylamino])-β-D-glucopyranoside (compound 3) as an amorphous solid: $^1H$ NMR ($CDCl_3$) δ0.88 (~t, 6H),, 1.1–1.7 (m, 46H), 1.44 (s, 3H), 1.53 (s, 3H), 2.25 (t, 2H, J=7.5 Hz), 2.42 (m, AB type, 2H), 3.30 (td, 1H, J=10, 5 Hz), 3.51 (m, 1H), 3.61 (~t, 1H, J=9 Hz), 3.75–4.0 (m, 3H), 4.58 (d, 1H, J=11.8 Hz), 4.69 (d, 1H, J=8.3 Hz), 4.88 (d, 1H, J=11.8 Hz), 5.06 (m, 1H), 5.97 (d, 1H, J=6.0 Hz), 7.33 (s, 5H).

(2) A solution of the compound 3 (0.74 g, 0.99 mmol), DMAP (0.012 g, 0.01 mmol) and pyridine (0.20 ml, 2.5 mmol) in $CH_2Cl_2$ (6 ml) was treated with 2,2,2-trichloroethyl chloroformate (0.15 ml, 1.1 mmol) and stirred at ambient temperature for 3 h. The reaction mixture was concentrated and the resulting residue taken up in 80% aqueous AcOH (15 ml) and heated at 60° C. for 1 h. Volatiles were removed under reduced pressure to give a syrup which was purified by flash chromatography (gradient elution, 50→55% EtOAc-hexanes) to give 0.71 g (81%) of benzyl 2-deoxy-2-[(R)-3-hexadecanoyloxytetradecanoylamino]-3-O-(2,2,2-trichloroethoxycarbonyl)-β-D-glucopyranoside (compound 4) as a colorless amorphous solid: $^1H$ NMR ($CDCl_3$) δ0.87 (~t, 6H), 1.1–1.15 (m, 46H), 2.22 (t, 2H, J=7.5 Hz), 2.29 (dd, 1H partly obscured by proceeding triplet, J=14.7, 5 Hz), 2.43 (dd, 1H, J=14.7, 5 Hz), 3.00 (br s, 2H), 3.45 (m, 1H), 3.75–4.15 (m, 4H), 4.55 (d, 1H, J=12 Hz), 4.7–4.9 (m, 4H), 5.0–5.15 (m, 2H), 6.34 (d, 1H, J=8.4 Hz), 7.28 (br s, 5H).

(3) To a solution of 2-(trimethylsilyl)ethyl 2-amino-2-deoxy-4,6-O-isopropylidene-β-D-glucopyranoside (compound 5, 6.46 g, 20.2 mmol) in $CHCl_3$ (300 ml) was added 1 N aqueous $NaHCO_3$ (300 ml) and 2,2,2-trichloroethyl chloroformate (8.5 g, 40 mmol). The resulting mixture was stirred vigorously for 3 h at room temperature. The organic layer was separated, dried ($Na_2SO_4$) and concentrated to give a colorless syrup. Flash chromatography on silica gel (gradient elution, 30→40% EtOAc-hexanes) afforded 9.6 g (96%) of 2-(trimethylsilyl)ethyl 2-deoxy-4,6-O-isopropylidine-2-(2,2,2-trichloroethoxycarbonylamino)-β-D-glucopyranoside (compound 6) as a colorless solid: mp 69–70° C.; $^1H$ NMR ($CDCl_3$) δ0.0 (s, 9 H), 0.94 (m, 2H, 1.44 and 1.52 (2s, 6H), 2.94 (br s, 1H), 3.23–3.37 (m, 2H), 3.48–3.62 (m, 2H), 3.79 (t, 1H, J=~10.5 Hz), 3.88–4.08 (m, 3H), 4.65 (d, 1H, J=8.3 Hz), 4.74 (m, 2H), 5.39 (d, 1H, J=7.4 Hz).

(4) A solution of compound 6 (7.5 g, 15.2 mmol), (R)-3-tetradecanoyloxytetradecanoic acid (7.58 g, 16.7 mmol) and 4-pyrrolidinopyridine (0.25 g, 1.7 mmol) in $CH_2Cl_2$ (95 ml) was treated with 1-(3-dimethylaminopropyl)-3-ethylcarbodiimide methiodide (EDC.MeI; 4.94 g, 16.7 mmol) and stirred for 16 h at room temperature. The reaction mixture was filtered through a short pad of CELITE®, concentrated, and the resulting residue was heated at 60° C. in 90% aqueous AcOH (100 ml) for 1 h. The mixture was concentrated and residual AcOH and water were removed by azeotroping with toluene (2×150 ml). The crude diol was purified by flash chromatography on silica gel (gradient elution, 30→40% EtOAc-hexanes) to give 11.8 g (83%) of 2-(trimethylsilyl)ethyl 2-deoxy-3-O-[(R)-3-tetradecanoyloxytetradecanoyl]-2-(2,2,2-trichloroethoxycarbonylamino)-β-D-glucopyranoside (compound 7) as an amorphous solid: $^1$H NMR (CDCl$_3$) δ0.0 (s, 9H), 0.9 (m, 8H), 1.1–1.7 (m, 42H), 2.30 (t, 2H, J=7.4 Hz), 2.52 (m, 2H), 3.36–3.72 (m, 4H), 3.78–4.03 (m, 3H), 4.57 (d, 1H, J=8.3 Hz), 4.65 (d, 1H, J=11 Hz), 4.77 (d, 1H, J=11 Hz), 5.0–5.15 (m, 2H), 5.20 (d, 1H, J=7.4 Hz).

(5) A solution of compound 7 (10.9 g, 12 mmol) and pyridine (2 ml, 25 mmol) in CH$_2$Cl$_2$ (125 ml) at 0° C. was treated dropwise over 15 min with a solution of 2,2,2-trichloro-1,1-dimethylethyl chloroformate (3.17 g, 13.2 mmol) in CH$_2$Cl$_2$ (25 ml). The reaction mixture was allowed to warm slowly to ambient temperature over 3.5 h. 4-Pyrrolidinopyridine (0.89 g, 6.0 mmol), N,N-diisopropylethylamine (10.5 ml 60 mmol) and diphenyl chlorophosphate (3.7 ml, 18 mmol) were added sequentially and the resulting mixture was stirred for 5 h at room temperature. The reaction mixture was diluted with CH$_2$Cl$_2$ (500 ml), washed with cold 7.5% aqueous HCl (2×250 ml), water (250 ml), saturated aqueous NaHCO$_3$ (250 ml), dried (Na$_2$SO$_4$), and then concentrated. The residue obtained was purified by flash chromatography on silica gel eluting with 12.5% EtOAc-hexanes to give 15.1 g (95%) of 2-(trimethylsilyl)ethyl 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-β-D-glucopyranoside (compound 8) as a viscous oil: $^1$H NMR (CDCl$_3$) δ0.0 (s, 9H), 0.8–1.0 (m, 8H), 1.1–1.65 (m, 42H), 1.83 and 1.90 (2s, 6H), 2.15–2.45 (m, 4H), 3.34 (q, 1H, J=~8 Hz), 3.37 (m, 1H), 3.81 (m, 1H), 3.95 (m, 1H), 4.27 (dd, 1H, J=12, 5 Hz), 4.34 (d, 1H, J=12 Hz), 4.58 (d, 1H, J=12 Hz), 4.66 (q, 1H, J=9 Hz), 4.86 (d, 1H, J=12 Hz), 5.03 (d, 1H, J=7.9 Hz), 5.21 (m, 1H), 5.54–5.70 (m, 2H), 7.2–7.8 (m, 10H).

(6) A solution of the compound 8 (6.5 g, 4.84 mmol) and dichloromethyl methyl ether (2.18 ml, 24.2 mmol) in CHCl$_3$ (60 ml) at 0° C. was treated with ZnCl$_2$ (1.0 M in ether; 2.41 ml, 2.41 mmol) and then allowed to warm slowly and stir at room temperature overnight. The reaction mixture was diluted with EtOAc, washed with saturated aq. NaHCO$_3$, dried (Na$_2$SO$_4$) and then concentrated. The light yellow oil obtained was purified by flash chromatography on silica gel eluting with 10% EtOAc-hexanes to give 5.4 g (88%) of 2-deoxy-4-O-diphenylphosphono-3-O-[(R)-3-tetradecanoyloxytetradecanoyl]-6-O-(2,2,2-trichloro-1,1-dimethylethoxycarbonyl)-2-(2,2,2-trichloroethoxycarbonylamino)-α-D-glucopyranosyl chloride (compound 9) as an amorphous solid: $^1$H NMR (CDCl$_3$) δ0.88 (~t, 6H), 1.1–1.6 (m, 42H), 1.78 (s, 3H), 1.88 (s, 3H), 2.18 (t, 2H, J=7.6 Hz), 2.34–2.52 (m, 2H), 4.2–4.4 (m, 4H), 4.70 (d, 1H, J=12 Hz), 4.73 (d, 1H, J=12 Hz), 4.83 (~q, 1H, J=9 Hz), 5.09 (m, 1H), 5.51 (~t, 1H J=10 Hz), 5.79 (d, 1H, J=8.0 Hz), 6.26 (d, 1H, J=3.6 Hz), 7.1–7.4 (m, 10H).

(7) A solution of the compound 4 (1.40 g, 1.54 mmol) and compound 9 (2.33 g, 1.85 mmol) in 1,2-dichloroethane (18.5 ml) was stirred with powdered 4 Å molecular sieves (1 g) for 1 h and then treated with AgOTf (1.43 g, 5.55 mmol) in one portion. The reaction was stirred at room temperature for 4 h shielded from light. An additional equivalent of AgOTf (0.475 g, 1.85 mmol) was then added and the reaction mixture was stirred overnight at ambient temperature. The resulting slurry was filtered and concentrated to give a nearly colorless oil. Flash chromatography on silica gel (gradient elution, 20→25% EtOAc-hexanes) afforded 2.40 g (73%) of benzyl 2-deoxy-6-O-[2-deoxy-4-O-diphenylphosphono-3-O-[(R)-3-tetradecanoyloxytetradecanoyl]-6-O-(2,2,2-trichloro-1,1-dimethylethoxycarbonyl-2-(2,2,2-trichloroethoxycarbonylamino)-β-D-glucopyranosyl]-3-O-(2,2,2-trichloroethoxycarbonyl)-2-[(R)-3-hexadecanoyloxytetradecanoylamino]-β-D-glucopyranoside (compound 10) as a colorless solid: mp 95–97° C.; $^1$H NMR (CDCl$_3$) δ0.88 (t, 12H, J=Hz), 1.1–1.65 (m, 88H), 1.84 (s, 3H), 1.90 (s, 3H), 2.15–2.47 (m, 8H), 3.06 (br s, 1H), 3.37–3.55 (m, 2H), 3.63–3.83 (m, 3H), 3.88 (dd, 1H, J=12, 3.5 Hz), 4.17 (dd, 1H, J=12, 2.5 Hz), 4.24 (dd, 1H, J=11, 5 Hz), 4.38 (d, 1H, J=11 Hz), 4.55–4.95 (m, 8H), 5.00 (m, 1H), 5.05–5.25 (m, 2H), 5.49 (~t, 1H, J=9 Hz), 5.89 (d, 1H, J=8.2 Hz), 5.93 (d, 1H, J=6.6 Hz).

(8) A stirred solution of the compound 10 (11.7 g, 5.53 mmol) in AcOH (250 ml) at 60° C. was treated with zinc dust (27.1 g, 0.415 mol) in three equal portions over 1 h. The reaction mixture was filtered through a bed of CELITE® and concentrated. The resulting residue was dissolved in EtOAc (500 ml), washed with 1 M aq. HCl (500 ml) and saturated aq. NaHCO$_3$ (500 ml), dried (Na$_2$SO$_4$) and then concentrated. A solution of the crude triol obtained and (R)-3-octadecanoyloxytetradecanoic acid (3.1 g, 6.08 mmol) in CH$_2$Cl$_2$ (60 ml) was treated with 2-ethoxy-1-ethoxycarbonyl-1,2-dihydroquinoline EEDQ, 2.26 g, 9.12 mmol) and stirred for 16 h at room temperature. The reaction mixture was concentrated in vacuo and the residue obtained was purified by flash chromatography on silica gel eluting with EtOAc-CHCl$_3$-AcOH (10:90:5) to give 6.4 g (56%) of benzyl 2-deoxy-6-O-[2-deoxy-4-O-diphenylphosphono-3-O-[(R)-3-tetradecanoyloxytetradecanoyl]-2-[(R)-3-octadecanoyloxytetradecanoylamino]-β-D-glucopyranosyl]-2-[(R)-3-hexadecanoyloxytetradecanolanino]-β-D-glucopyranoside (compound 11) as a colorless syrup.

(9) A solution of the compound 11 (6.3 g, 3.07 mmol) in a mixture of AcOH (25 ml) and THF (250 ml) was hydrogenated in the presence of palladium black (3.5 g) at room temperature and 65 psig for 18 h. After removal of the catalyst by filtration, platinum oxide (3.0 g) was added and the hydrogenolysis was continued under the same conditions for 24 h. The catalyst was collected, rinsed with CHCl$_3$, and the combined filtrate and rinsings were concentrated. Flash chromatography on silica gel eluting with chloroform-methanol-water-triethylamine (90:10: 1:1) afforded 3.9 g of material which was dissolved in cold 2:1 CHCl$_3$-MeOH (500 ml) and washed with cold 0.1 N aq. HCl (200 ml). The lower organic layer was filtered through No. 4 Whatman filter paper and concentrated in vacuo to give 3.6 g (65%) of the free acid. A portion of the free acid was lyophilized from 2% aq. triethylamine to give pure 2-deoxy-6-O-[2-deoxy4-O-phosphono-3-O-[(R)-3-tetradecanoyloxytetradecanoyl]-2-[(R)-3 -octadecanoyloxytetradecanoylamino]-β-D-glucopyranosyl]-2-[(R)-3-hexadecanoyloxytetradecanoylamino]-D-glucopyranose Triethylammonium salt (compound 1) as a white solid: mp 174–175° C. (dec); IR (film) 3306, 2920, 2851, 1732, 1652, 1552, 1467, 1378, 1308, 1178, 1060, 953, 845, 721 cm$^{-1}$; $^1$H NMR (CDCl$_3$-CD$_3$OD) δ0.88 (~t, 18H), 1.15–1.7 (m, 147H), 2.25–2.7 (m, 12H), 3.07 (q, 6H, J=7.4 Hz), 3.22–4.3 (m, 12H), 4.69 (d, 1H, J=8.0 Hz), 5.05–5.25 (m, 5H), 6.69 (d, 1H J=8.5 Hz), 7.41 (d, 1H, J=8.5 Hz); $^{13}$C NMR (CDCl$_3$) δ174.0, 173.4, 170.8, 170.5, 100.1, 91.4, 75.7, 72.7, 71.8, 71.1, 71.0, 70.6, 61.0, 54.9, 54.0, 45.6, 41.7, 41.1, 39.3, 34.5, 32.0, 29.8, 29.5, 29.4, 25.4, 25.1, 22.7, 14.2, 8.6.

Anal. Calcd. for C$_{108}$H$_{208}$N$_3$O$_{21}$P.5H$_2$O: C, 64.67; H, 10.95; N, 2.09; P, 1.54. Found: C, 64.58; H, 10.63; N, 2.12; P, 1.58.

EXAMPLE 2

Cardioprotective Effect of L34 on Infarct Size in the Dog

Pretreatment of dogs with the compound of the subject invention prior to ischemia/reperfusion significantly reduced infarct size when compared to controls. Animals treated with L34 either 10 min or 24 h prior to a one hour left anterior descending coronary artery (LAD) occlusion and 3 h of reperfusion showed a reduced infarct size as expressed as a percentage of the area at risk. Further, administration of aminoguanidine, a selective inhibitor of inducible nitric oxide synthase, blocked the delayed cardioprotective effect of L34 observed in treated animals.

Adult mongrel dogs of either sex, weighing 19.0–30.0 kg were fasted overnight, anaesthetized with intravenous sodium barbital (200 mg/kg) and sodium pentobarbital (15 mg/kg), and ventilated with room air supplemented with 100% oxygen at an end expiratory pressure of 5–7 cm $H_2O$ to prevent atelectasis. Arterial blood pH $PO_2$ and $PCO_2$ were monitored at selected intervals by an automatic blood gas system and maintained within a normal physiological range (pH 7.35–7.45, $PO_2$ 10.6–16.0 kPa, $PCO_2$ 3,3–4.7 kPa) by adjusting the respiratory rate and oxygen flow and by an infusion of 1.5% sodium bicarbonate when necessary. Body temperature was maintained at 38±1° C. by using a heating pad.

A double pressure-transducer-tipped catheter was inserted into the aorta and left ventricle via the left carotid artery for measurements of aortic and left ventricular pressure. Left ventricular dP/dt was determined by electronic differentiation of the left ventricular pressure pulse.

A left thoracotomy was performed at the fifth intercostal space. The lung was retracted, the pericardium incised, and the heart suspended in a cradle. A 10–15 mm segment of the left anterior descending coronary artery (LAD) was dissected from surrounding tissue. A calibrated electromagnetic flow probe was placed around the LAD to determine coronary blood flow. The left atrial appendage was cannulated for radioactive microsphere injections to determine regional myocardial blood flow to the ischemic and normal areas during reperfusion. Electrodes were attached to the left atrial appendage to pace the heart at 150 beats/min with an electronic stimulator (Grass SD9) when the heart rate dropped below 140 beats/min.

Animals were randomly assigned to five groups; those receiving 35 μg/kg drug 24 h intravenously before occlusion (24 h), those receiving 35 μg/kg drug 24 h before occlusion and 30 mg/kg aminoguanidine subcutaneously 60 min before occlusion, those receiving 70 μg/kg drug 10 min before occlusion (10 min), those receiving 30 mg/kg aminoguanidine 60 min before occlusion and vehicle controls. Hemodynamic variables were monitored and recorded throughout the experiment. The phosphoglycolipid of the subject invention, L34, formulated in 40% propylene glycol and 10% ethanol (tEOH) in Water for Injection (WFI) was diluted one to one in 5% dextrose in water (D5W) and injected as an intravenous bolus 24 h or 10 min before the experiment. The control group was treated with an equivalent volume of vehicle (40% propylene glycol, 10% EtOH in WFI diluted in D5W). All dogs were subjected to a 60 min period of LAD occlusion followed by 3 h of reperfusion.

Regional myocardial blood flow was measured by the radioactive microsphere technique. Microspheres were injected at 5 min and 30 min of coronary artery occlusion, as well as at the end of the reperfusion period. Carbonized plastic microspheres (15 μm diameter, New England Nuclear) labeled with $^{141}C$, $^{103}Ru$, or $^{95}Nb$ were suspended in isotonic saline with 0.01% Tween 80 added to prevent aggregation. The microspheres were ultrasonicated for 5 min and vortexed for another 5 min before administration. One ml of the microsphere suspension (2–4×$10^6$ spheres) was given via the left atrial catheter and flushed by 5 ml of saline. A reference blood flow sample was withdrawn from the femoral artery at a constant rate of 6.6 ml/min immediately before microsphere injection.

At the end of the reperfusion, the LAD was cannulated and 10 ml of Patent Blue dye and 10 ml of saline were injected at equal pressure in the left atrium and LAD, respectively, to determine anatomic area at risk (AAR) and the non-ischemic area. The heart was then fibrillated electrically (20 V, 250 Hz square wave pulses applied directly to the left ventricle) and removed immediately. The left ventricle was dissected and sliced into serial transverse sections 6–7 mm in width, from apex to base. The non-stained ischemic area and the blue stained normal area were separated and both regions incubated at 37° C. for 30 min in 1% 2,3,5-triphenyltetrazolium chloride (TTC) in 0.1 M phosphate buffer adjusted to pH 7.4 TTC stains the non-infarcted myocardium a brick red color indicating the presence of a formazin precipitate that results from the reduction of TTC by dehydrogenase enzyme present in viable tissue. Area at risk was expressed as percentage of the left ventricle and infarcted tissue was expressed as a percentage of area at risk. The weights of left ventricle, area at risk, and infarcted tissue were measured by a gravimetric method.

Transmural tissue slices were sectioned into subepicardium, mid-myocardium, and subendocardium of non-ischemic (three pieces) and ischemic regions (five pieces) and the tissue samples weighed (0.3–0.8 g). Transmural pieces were obtained from the center of the ischemic area and were at least 1 cm from the perfusion boundaries as indicated by the Patent Blue dye. All samples were counted in a gamma counter to determine the activity of each isotope in each sample. The activity of each isotope was also determined in the reference blood flow samples. Myocardial blood flow was calculated by using a preprogrammed computer to obtain the true activity of each isotope in individual samples, and tissue blood flow was calculated from the equation $Q_m = Q_r \times C_m/C_r$ where $Q_m$ is myocardial blood flow(ml/min/g). $Q_r$ is the rate of withdrawal of the reference blood flow (6.6 m/min), $C_r$ is the activity of the reference blood flow sample (count/min), and $C_m$ is the activity of the tissue sample (counts/min/g). Transmural blood flow was calculated as the weighted average of the three layers in each region. The results are summarized in Table 1 below.

TABLE 1

| Group | N | IS/AAR(%) | Transmural Collateral (Blood Flow) ml/min/g |
|---|---|---|---|
| L34 (24 h) (35 μg/kg) | 7 | 13.3 ± 2.2%* | 0.06 ± 0.01 |
| L34 (10 min) (70 μg/kg) | 7 | 15.0 ± 3.0%* | 0.05 ± 0.01 |
| L34 (24 h) (35 μg/kg) + AG (30 mg/kg) | 9 | 25.2 ± 2.7% | 0.06 ± 0.01 |
| AG (30 mg/kg) | 7 | 22.4 ± 2.8% | 0.07 ± 0.02 |
| Vehicle | 10 | 26.8 ± 2.4% | 0.07 ± 0.01 |

All values are the mean ± standard error of the mean.
*P > 0.05 vs control group.
Abbreviations;
IS = infarct size;
AAR = area at risk.

Transmural collateral blood flow expressed in ml/min/g were not significantly different among treatment groups.

Vehicle infarct size average was 26.8±2.4%. Infarct size in animals administered the compound of the subject invention either 10 min or 24 h before occlusion were 15.0±3.0% and 13.3±2.2%, respectively. Pretreatment of dogs with the compound of the subject invention prior to ischemia/reperfusion significantly reduced infarct size when compared to controls. Infarct size reduction in animals administered the subject compound 24 h before occlusion was blocked by aminoguanidine resulting in an average infarct size of 25.2±2.7%.

EXAMPLE 3

Cardioprotective Effect of L34 on Infarct Size in Rabbits

Pretreatment of rabbits with the compound of the subject invention prior to myocardial ischemia/reperfusion significantly reduced infarct size when compared to vehicle controls. Animals treated with L34 24 h prior to a 30 min occlusion of the first large anteriolateral branch of the circumflex artery, or the circumflex artery itself, followed by 3 h of reperfusion showed a reduced infarct size expressed as a percentage of the area at risk (IS/AAR %).

Male New Zealand white rabbits weighing 2.5–3.5 kg were injected with vehicle or L34 24 h before the experiment. L34 was formulated in vehicle composed of 40% propylene glycol, 10% ethanol in water. For the experiment, animals were intramuscularly anesthetized with ketamine (35 mg/kg) and xylazine (5 mg/kg). Tracheotomy was performed and the animals intubated with a cuffed endotracheal tube (Portex, 4.0 mm internal diameter) and then mechanically ventilated with room air on a positive pressure respirator Q Industries, Mobile, Ala.). Ventilatory rate was 27–35 breaths per min, and tidal volume was approximately 10–17 ml. The respiratory rate was frequently adjusted as needed to maintain $pO_2$ greater than 100 mm Hg, $pCO_2$ at 35–45 mm Hg, and pH 7.35–7.45. After the left jugular vein was isolated and cannulated with a polyethylene (PE) catheter, 0.9% sodium chloride (0.15 ml/min) was continuously administered during the experiments. The carotid artery was dissected out and a fluid-filled PE tube (PE-50) was placed in it and connected immediately to a multichannel polygraph recorder via pressure transducer for arterial pressure recording. The EKG was recorded throughout the experiment via lead II of the standard elctrocardiogram. A left thoracotomy was performed through the fourth intercostal space, and the pericardium was opened to expose the heart. A silk thread was passed around the large marginal branch of the circumflex artery midway between the atrioventricular groove and the apex with a taper needle, and the ends of the tie were threaded through small vinyl tube to form a snare. The first anteriolateral branch of the left circumflex coronary artery between the atrio-ventricular groove and the apex of the heart was occluded by pulling the snare, which was then fixed by clamping the tube with a mosquito hemostat. The rabbits were given 500 units/kg sodium heparin to prevent thrombus formation around the snare. Myocardial ischemia was confirmed by regional cyanosis, ST elevation and decreased blood pressure. Reperfusion was confirmed by hyperemia over the surface after releasing the snare.

At the end of each experiment, the ligature around the large marginal branch of the circumflex artery was retightened to reocclude the artery and approximately 4 ml of 10% Evans blue dye was injected into the jugular vein until the eyes turned blue. The dye delineates the area of the myocardium at risk for infarction from the perfused area (non risk area). The rabbits were sacrificed, and their hearts harvested and cut into six transverse slices of equal thickness. The area at risk was determined by negative staining and calculated as a percentage of the portion of left ventricle containing the risk area (AAR/LV %) and infarct size as a percentage of area at risk (IS/AAR %). The slices were stained by incubation for 20 min in 1% triphenyl tetrazolium chloride in isotonic phosphate buffer pH 7.4. Viable myocardium stains red while nonviable or infarcted tissue remains pale or colorless. Regions of infarcted tissue and the risk zone were determined by computer morphometry using Bioquant imaging software and the percentage of infarcted area and risk area calculated.

Figure 2:
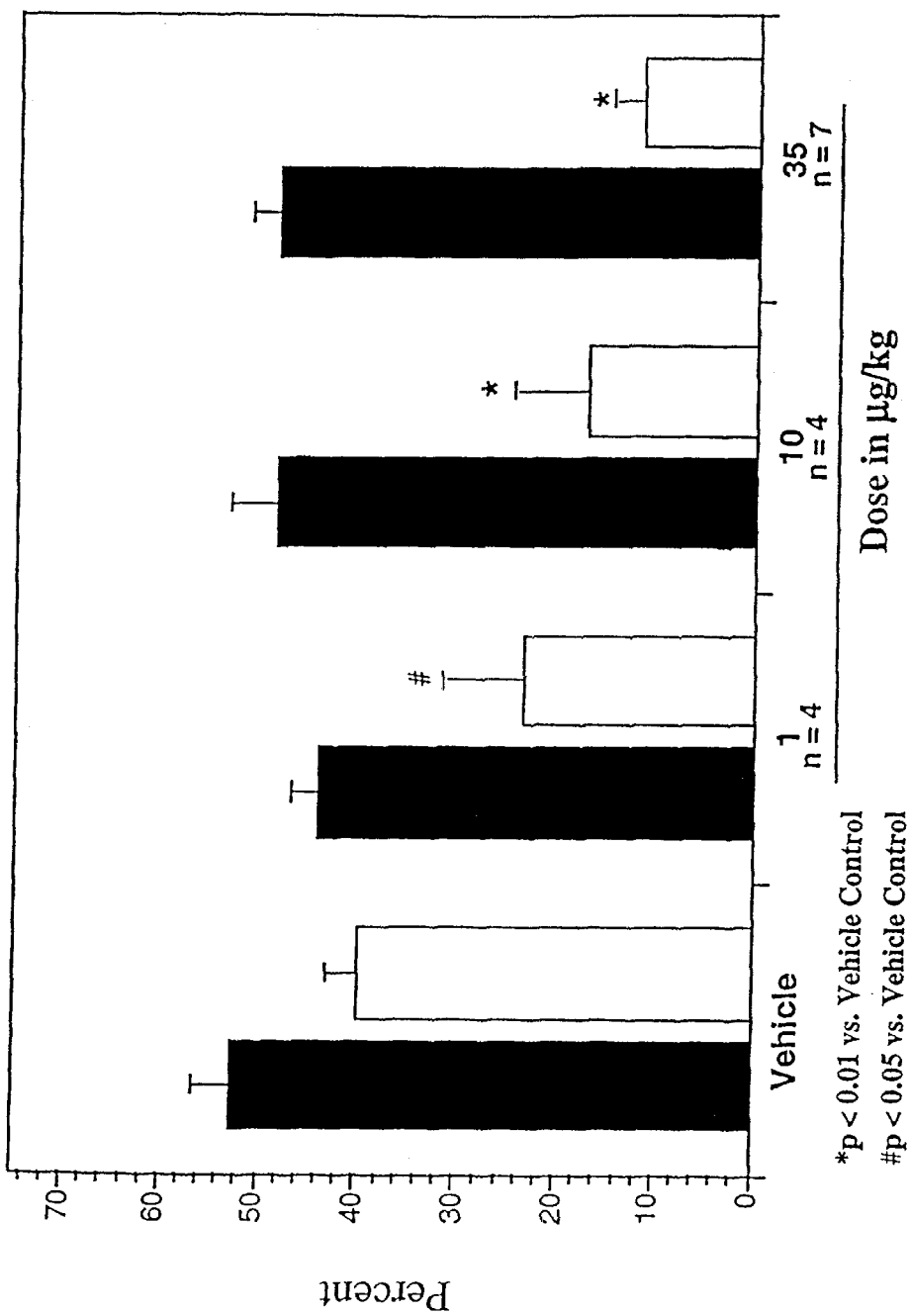
FIG. 2 shows the dose response of the cardioprotective effect of the compound against infarction given 24 h before ischemia of the subject invention in the rabbit model. ■ % Left Ventricle at Risk; □ % Infarct in Risk Area; # p<0.05 vs. Vehicle Control; * p<0.01 vs. Vehicle Control.

FIG. 1 shows that animals treated with the compound of the subject invention had an approximately 70% reduction in infarct size expressed as a percentage of the area at risk when compared to controls. FIG. 2 shows the impact of L34 on infarct size in a dose response curve with greater than a 50% reduction in infarct size observed at doses of 10 to 35 μg/kg.

EXAMPLE 4

Cardioprotective Effect of L34 on Infarct Size in Dogs with Drug Infusion

Treatment of dogs with the compound of the subject invention (L34) prior to ischemia/reperfusion significantly reduced infarct size when compared to vehicle controls. Animals treated with a bolus of L34 followed by continuous infusion of the drug beginning 3 h prior to occlusion with administration continuing through 1 h of ischemia and 1 h of a 3 h reperfusion period showed a reduced infarct size expressed as a ratio of area of necrosis (AN) relative to the area at risk (AR). Animals treated with only a bolus of L34 3 hours before ischemia showed no protection.

Mongrel dogs weighing 16–24 kg were randomly assigned to one of four groups: vehicle control; L34 high dose bolus plus infusion; L34 low dose bolus plus infusion and L34 bolus only. Animals in the L34 high dose bolus plus infusion group received an intravenous bolus injection of 70 μg/kg L34 formulated in vehicle (40% propylene glycol and 10% ethanol in water) and diluted in 5% dextrose in water to a final volume of 10 ml immediately followed by 40 μg/kg/h infusion of the drug beginning three hours prior to occlusion. The low dose bolus plus infusion group of dogs were bolus dosed with 35 μg/kg of drug followed immediately thereafter by infusion of drug at a dose of 4.0 μg/kg/h. With both dosing protocols, infusion of the drug continued through the 1 h occlusion and 1 h into the 3 h reperfusion. Animals in the bolus only group were given a 70 μg/kg bolus dose of L34 3 h before occlusion. Dogs assigned to the vehicle control group received a weight-adjusted and diluted "dose" of vehicle.

All dogs were anesthetized with pentobarbital sodium (30 mg/kg iv), intubated, and ventilated with room air. The left jugular vein and left carotid artery were cannulated for administration of fluids and drugs and to monitor heart rate and arterial pressure, respectively. The heart was then exposed through a left lateral thoracotomy and suspended in a pericardial cradle. A fluid-filled catheter was positioned in the left atrium for later injection of radio labeled microspheres ($^{141}$Ce, $^{103}$Ru, or $^{95}$Nb) for measurement of regional myocardial blood flow (RMBF). A segment of the left anterior descending coronary artery (LAD) was isolated, usually distal to its first major diagonal branch, as the site of later coronary occlusion.

After stabilization, animals underwent a 60 min period of occlusion. Heart rate and arterial pressures were monitored at baseline, immediately before the sustained occlusion, and at 10 min after the onset of occlusion. All dogs received a prophylactic dose of lidocaine (1.5 mg/kg iv bolus), and the LAD was ligated. The severity of ischemia was assessed in all dogs by measurement of RMBF at 10 min after the onset of LAD occlusion.

At the end of 3 h reperfusion the LAD was reoccluded and UNISPERSE® blue pigment (0.25–0.5 ml/kg) was injected into the coronary vasculature via the left atrial catheter to delineate the in vivo boundaries of the occluded LAD bed, and, with animals under deep anesthesia, cardiac arrest was produced by intracardiac injection of KCl. The hearts were rapidly excised. The heart was sliced into serial transverse sections from apex to base and incubated in TTC stain to detect viable and necrotic tissue within the ischemic zone of myocardium. After fixation, tissue blocks were cut from the center of the previously ischemic LAD bed and the remote, normally perfused circumflex bed and divided into subendocardial and mid- and subepicardial segments. RMBF was then quantified using standard methods.

Figure 3:
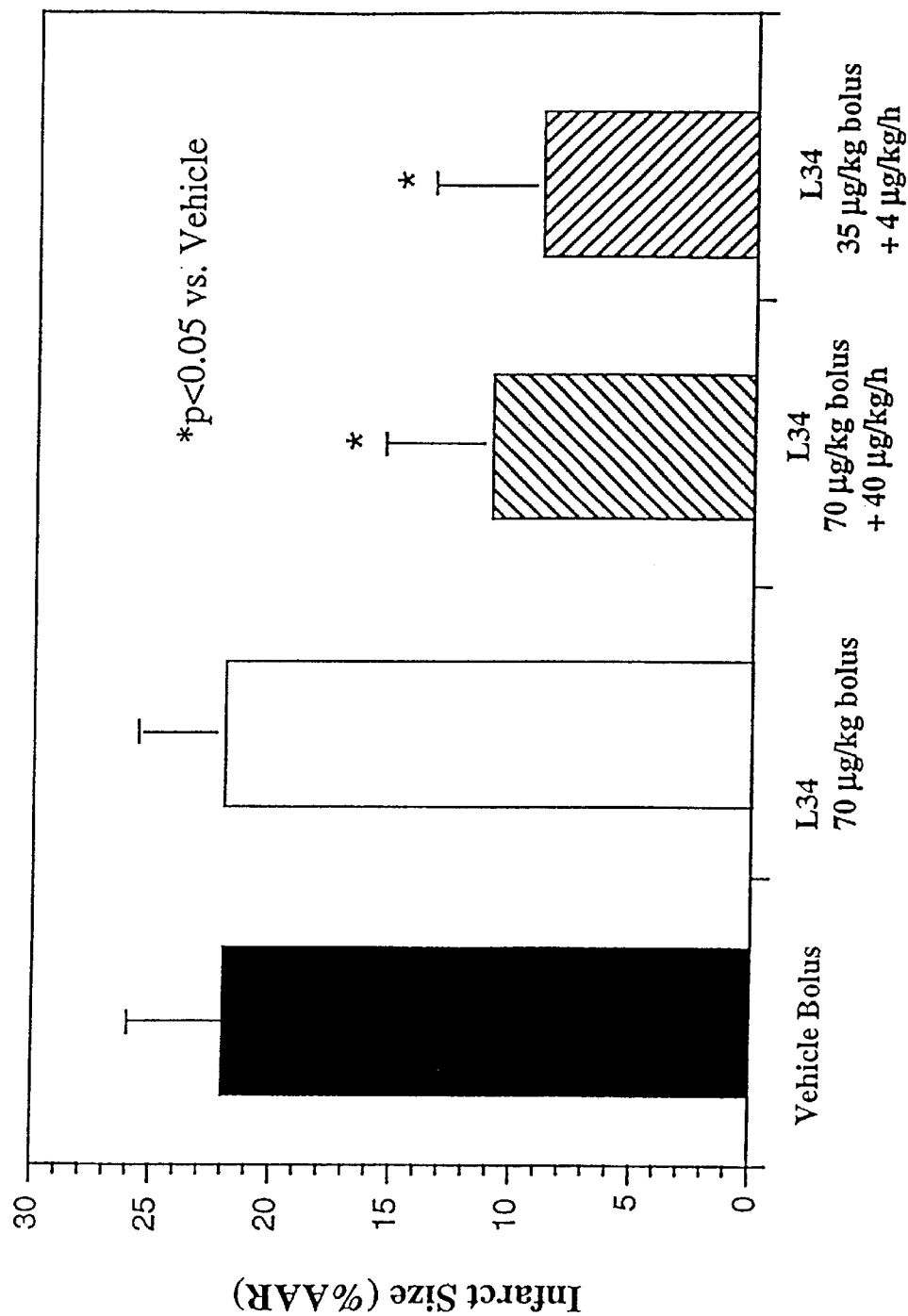
FIG. 3 shows the early cardioprotective effect of the compound of the subject invention against infarction is extended for 3 h after bolus dosing in dog models by infusion with the compound. Animals were infused with L34 after bolus dosing for 3 h before occlusion, through a 1 hour occlusion and 1 h into a 5 h reperfusion. ■ Vehicle; □ L34 bolus only, ▨ L34 bolus (70 μg/kg) plus infusion (40 μg/kg); ▧ L34 bolus (35 μg/kg) plus infusion (4 μg/kg).

FIG. 3 shows animals treated with a bolus of L34 followed by infusion with the drug beginning 3 h prior to ischemia displayed a statistically significant reduction in infarct size as reported as a ratio of area necrosis (AN) to area at risk (AR). Dogs treated only with a bolus of L34 3 h prior to occlusion showed no reduction in infarct size which when considered in light of the results presented in example 2 and 5 (below), suggest that the cardioprotective activity of L34 observed immediately after bolus dosing (10 min) has dissipated by 3 h following bolus dosing. These data also demonstrate the acute cardioprotective effect of the drug can be sustained for at least 3 h by infusing a treated animal with the drug immediately following bolus dosing.

EXAMPLE 5

Cardioprotective Effect of L34 on Infarct Size in Pigs

Pretreatment of pigs with the compound of the subject invention prior to ischemia/reperfusion significantly reduced infarct size when compared to controls. Animals treated with L34 10 min prior to a 40 min left anterior descending coronary artery (LAD) occlusion and 3 h of reperfusion showed a reduced infarct size as expressed as a percentage of the area at risk in grams.

To assess the efficacy of L34 to reduce infarct size, nine pigs were assigned in a non-blinded fashion to one of four groups: (1) control (n=2), (2) vehicle control (n4), (3) L34 (35 µg/kg) (n=2), (4) L34 (70 µg/kg) (n=1). L34 was formulated in 10% ethanol, 40% propylene glycol in Water for Injection. Blinded studies were additionally conducted with eight pigs randomly assigned to one of two treatment groups: (1) A (n=4), (2) B (n=4). Group A and B were either vehicle control or L34. Vehicle or drug injection was diluted one to one with 5% dextrose in Water for Injection prior to administration.

Male pigs (15–20 kg) were anesthetized with ketamine (25 mg/kg, i.m.) and sodium pentobarbital (10 mg/kg, i.v.), intubated and mechanically ventilated with room air. Pigs were placed on a 37° C. circulating water heating pad. The left carotid artery of each animal was cannulated with 5Fr Millar catheter for measuring left ventricular pressure and the right carotid artery was cannulated with 24G I.V. catheter for sampling blood. A median sternotomy was performed and the pericardium was incised. The left anterior descending artery was identified and a 4-O suture was placed just distal to the first diagonal branch. The ends of the suture were passed through small plastic tubes to form a snare.

After the animals equilibrated, baseline hemodynamic and blood sample were taken, L34 (35 µg/kg) was administered intravenously 10 min prior to coronary artery occlusion. Myocardial regional ischemia was induced by pulling the ends of the snare and tightening the snare using a hemostat.

Following 40 min of occlusion, the snare was released and the myocardium was reperfused for 3 h. The hemodynamic parameters at certain time points were recorded and blood samples were collected.

At the end of the protocol, the coronary artery was reoccluded, 8 ml of a 50% solution of UNISPERSE® blue dye (Dupont, DE) was injected into the left atrium and 0.8 ml of 1% triphenyltetrazolium chloride (TTC) was injected into the coronary artery just distal to occluded point. The heart was excised and frozen at −70° C. overnight, then was thawed and cut into 2 mm thick transverse slices with an electric slicer (Rival, MO). Each slice was weighed and scanned to measure the area of unstained tissue (the infarct area) and the tissue stained red by TTC dye (area at risk) using a Power Mac 7300 computer (Apple, CA) and an HP ScanJet 5p Scanner (Hewlett Packard, CA).

Figure 4:
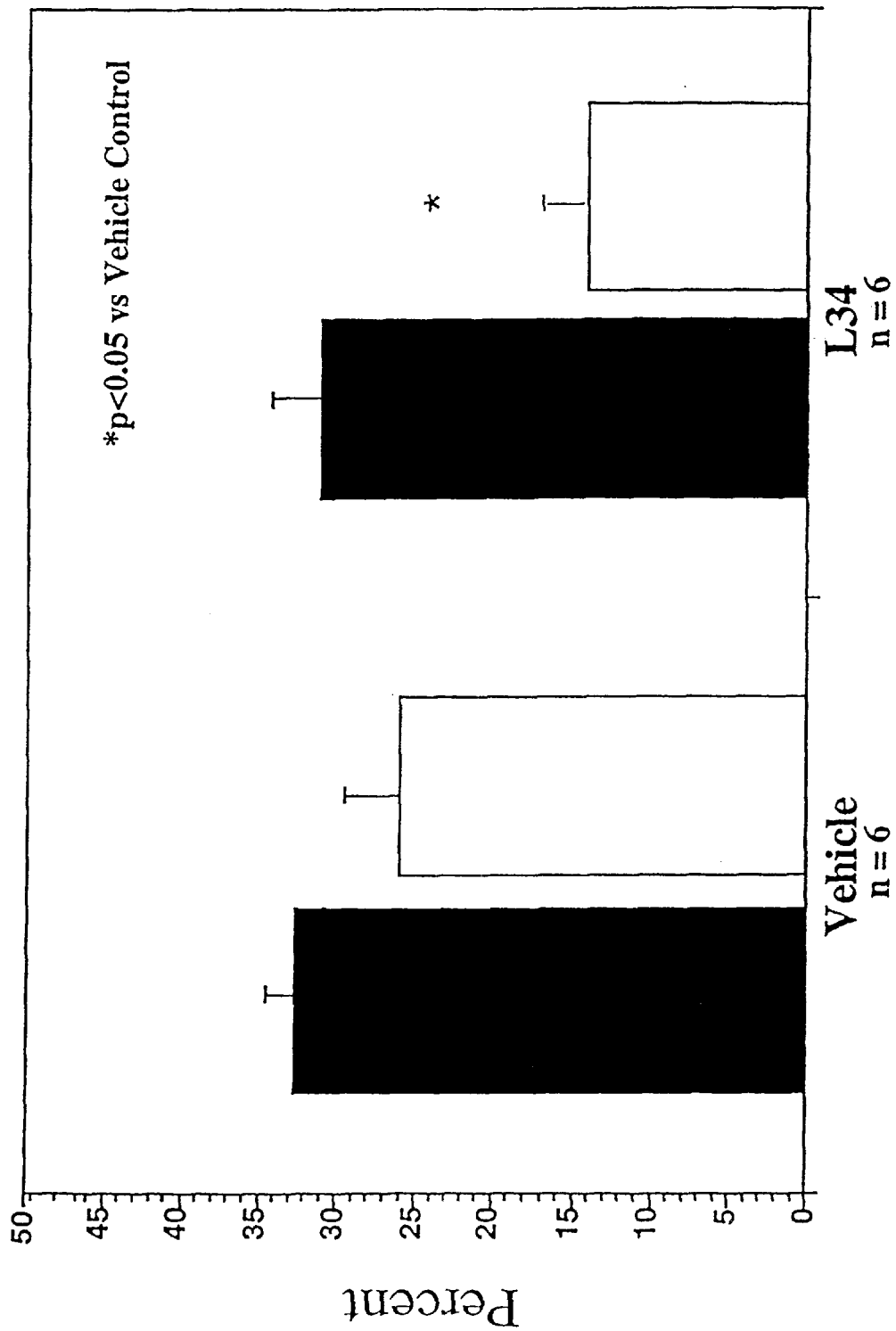
FIG. 4 shows the cardioprotective effect of the compound of the subject invention against infarction given 10 min before ischemia in a pig model of regional myocardial ischemia/reperfusion. ■ % Left Ventricle at Risk; □ % Infarction Risk Area.

FIG. 4 shows that treatment with the compound of the subject invention gave a 46% reduction in infarct size expressed as % AN/AR in g when compared to controls.

EXAMPLE 6

Cardioprotective Effect of L34 on Myocardial Stunning in Dogs

The compound of the subject invention provided both an acute and delayed protective effect against cardiac stunning in dogs. Pretreatment of dogs with the compound of the subject invention 10 minutes and 24 hours prior to ischemia produced significant improvement in the recovery of regional segment shortening (%SS) in the ischemic-reperfused myocardium of anesthetized dogs subjected to a multiple ischemia/reperfusion stunning protocol. Dogs were subjected to five 5-minute periods of coronary artery occlusion interspersed with 10 minute periods of reperfusion and finally followed by 2 hours of reperfusion. Regional systolic shortening in the subendocardium of the ischemic area was determined by sonomicrometry by placing a set of piezoelectric crystals in the subendocardium approximately 10–15 mm apart. Regional myocardial blood flow was determined by the radioactive microsphere technique during the first 5 min occlusion period and at the end of 2 h of reperfusion. Hemodynamics and blood gases were also measured at various times throughout the experiment. There was no significant differences between the control and pretreated groups in body weight, left ventricular weight, area at risk weight or the area at risk as a % of the left ventricle. Further, no important differences were evident between the groups in regional myocardial or transmural blood flows in the nonischemic or ischemic region during the first occlusion period or at 2 h of reperfusion. All groups, therefore, were subjected to similar degrees of ischemia during the first occlusion period and had similar reflows during the reperfusion period. The mean arterial blood pressure and rate pressure-product were significantly ($p<0.05$) higher at baseline in the dogs pretreated 10 min prior to occlusion with L34 as compared to the control group, there were however no significant differences between groups observed throughout the remainder of the experimental protocol. In addition, the blood gases were not different between groups.

Figure 5:
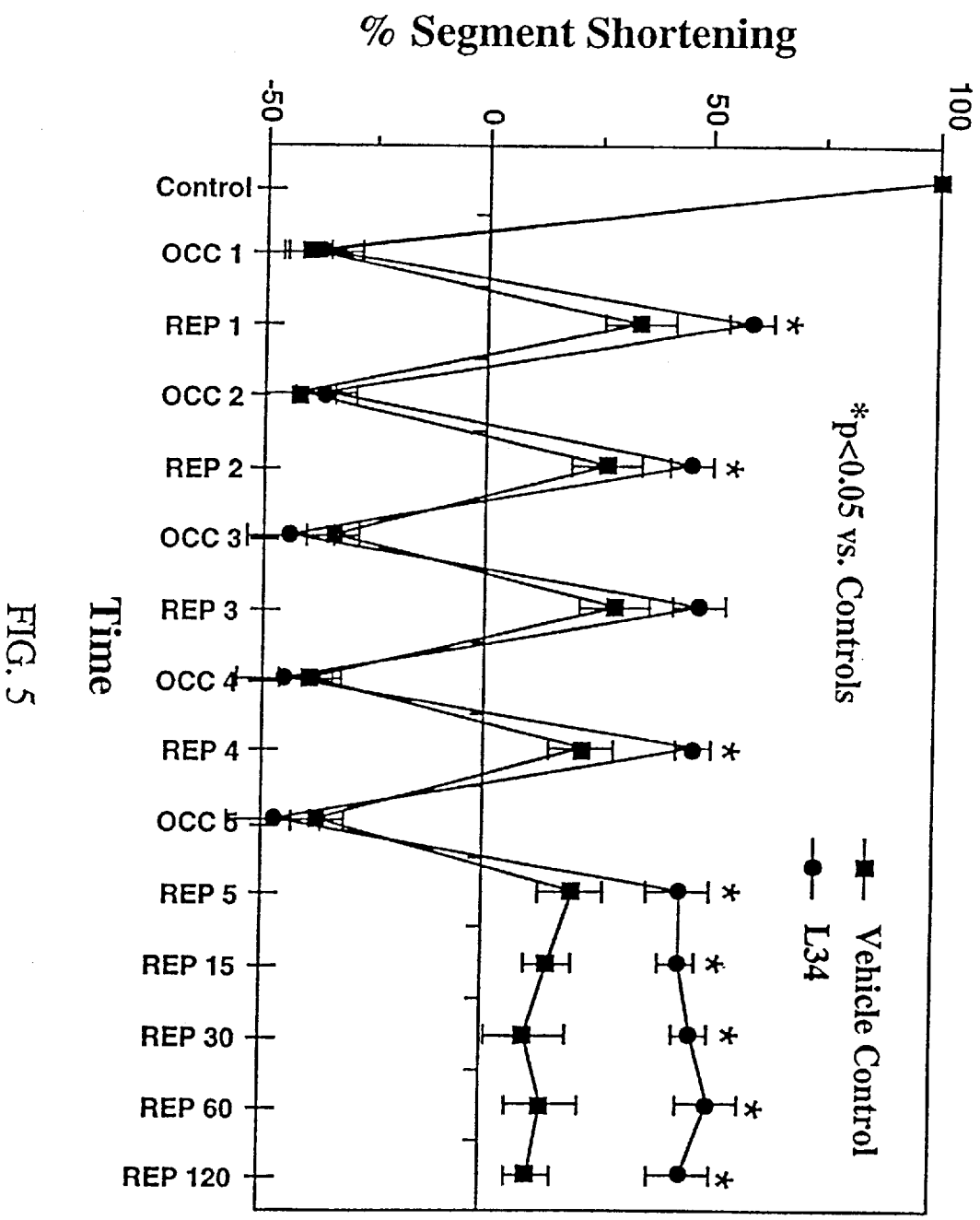
FIG. 5 shows the cardioprotective effect of the compound of the subject invention against reversible contractile dysfunction or stunning given 10 min before ischemia in a canine model of repetitive transient regional ischemia. ■ Vehicle Control; ● 34.
Figure 6:
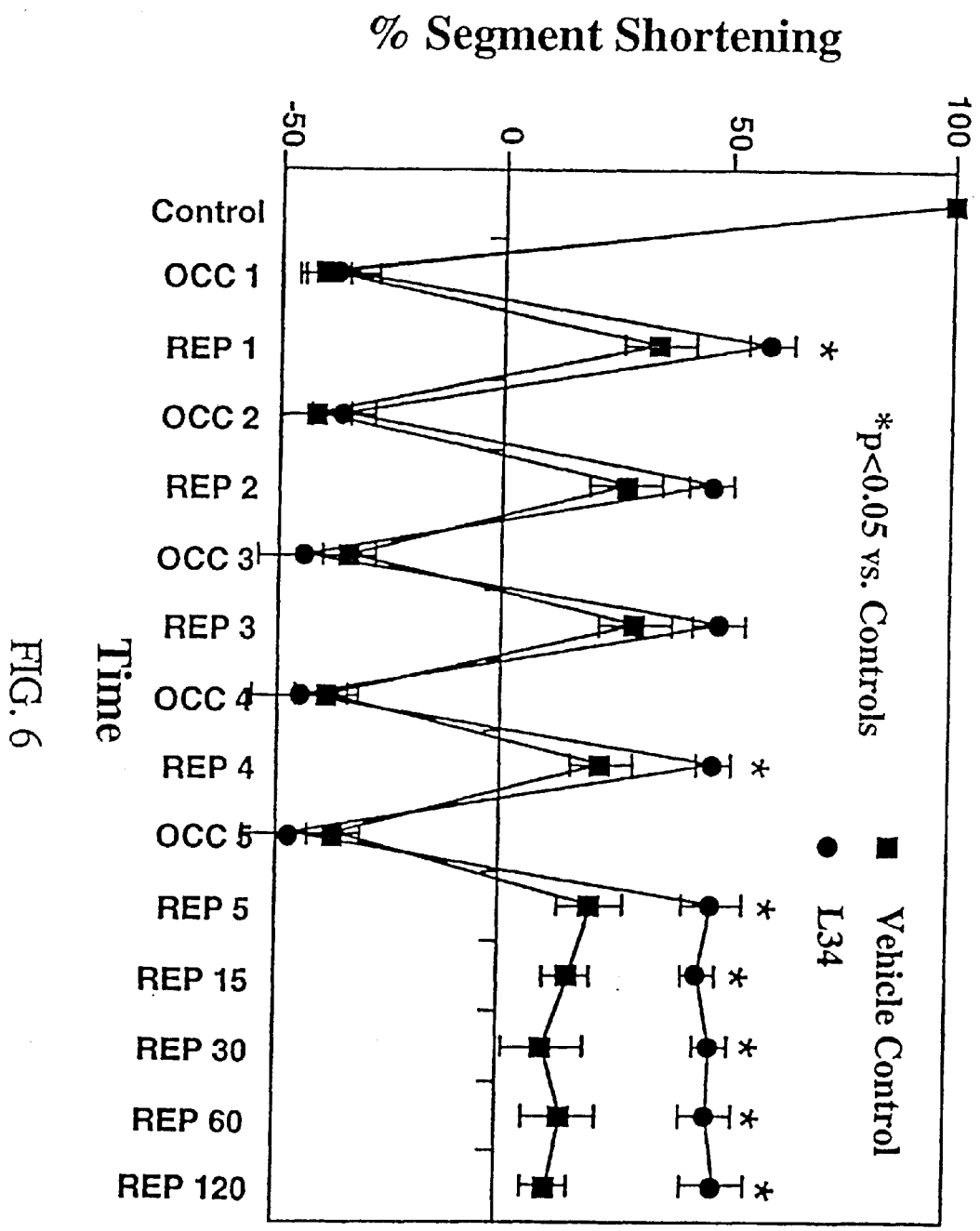
FIG. 6 shows the cardioprotective effect of the compound of the subject invention against reversible contractile dysfunction or stunning given 24 h before ischemia in a canine model of repetitive transient regional ischemia. ■ Vehicle Control; ● L34.

Pretreatment with L34 10 min prior to the first occlusion period resulted in a significantly greater recovery of regional wall motion (%SS) following the first, second and fourth occlusion periods and at all times sampled during the final 2 h reperfusion period as compared to the control group (FIG. 5). Similarly, 24 h pretreatment with L34 also resulted in a significantly greater recovery of regional wall motion (%SS) following the first and fourth occlusion period and at all times measured during the final 2 hour reperfusion period as compared to the control group (FIG. 6).

EXAMPLE 7

Effect of L34 on TNF-α and IL-8 Secretion in THP-1 Cells

The human myelomonocytic cell line THP-1 is commonly used for the analysis of the proinflammatory status of various compounds. THP-1 cells (American Type Culture Collections Cat. No. 202-TIB) were grown in RPMI 1640, 10% heat inactivated fetal bovine serum (FBS) and $2 \times^{-5}$ M β-mercaptoethanol to a cell density of between $4 \times 10^5$/ml and $7 \times 10^5$/ml. Cells were removed from culture and resuspended at $1 \times 10^6$ cells/ml in RPMI 1640 containing 5% fetal bovine serum. Resuspended cells were then pipetted into sterile, disposable polystyrene 150×25 mm petri dishes and treated with the natural maturational agent 1α, 25-dihyroxyvitamin $D_3$ at $1 \times 10^{-7}$ M between 24 and 72 hours depending on the degree of maturation desired. These maturationally "pretreated" cells were then washed 3× in RPMI 1640 containing more than 2% but less than 10% fetal bovine serum. After the third wash cells were resuspended in RPMI 1640 containing 5% FBS plus 2% human AB sera (Irvine Scientific) at $5 \times 10^5$ cells/ml and transferred at 2 ml per well in a tissue culture grade, flat bottom polystyrene 24 well plate. After incubation with various concentrations of L34, culture supernatants were collected by centrifugation at 4, 16 and 24 hours of drug exposure, aliquoted and stored at −70° C. until tested for proinflammatory cytokines. Cytokine concentration in the THP-1 culture supernatants were quantified using standard human cytokine ELISA kits from R&D Laboratories. The assays were performed according to manufacture's instructions. L34 did not induce detectable TNF-α or IL-8 secretion by THP-1 cells at any concentration between 1 ng/ml and 10 μg/ml.

EXAMPLE 8

Effect of L34 on the Fever Response in Rabbits

The compound of the subject invention was evaluated for pyrogenicity using a standard three rabbit USP pyrogen test (NAMSA, Northwood Ohio) at dose levels between 10 and 1000 μg/kg. Three rabbits were intravenously administered the compound in 40% propylene glycol and 10% ethanol in water at varying doses diluted one to one in D5W prior to dosing. Each animal's body temperature was monitored over the course of 4 h. Pyrogenic doses and borderline pyrogenic doses were defined by established USP definitions. Any temperature decrease was recorded as a rise of zero. An individual rise in temperature of less than 0.5° F. was considered non-pyrogenic. A borderline pyrogenic dose was a dose where at least one of three rabbits had a peak temperature rise of ≧0.5° C. above baseline over three hours postdosing.

Results of this test are shown in Table 2. Desirably, the compound of the subject invention was not pyrogenic at any of the doses tested.

TABLE 2

Pyrogenicity of L34

| L34 Dose μg/kg | | | | | |
|---|---|---|---|---|---|
| 10 | 20 | 30 | 40 | 60 | 80 |
| Average Temperature Rise | | | | | |
| 0.14 | 0.17 | 0.17 | 0.00 | 0.10 | 0.13 |

| L34 Dose μg/kg | | | | | | |
|---|---|---|---|---|---|---|
| 120 | 160 | 240 | 360 | 480 | 500 | 1000 |
| Average Temperature Rise | | | | | | |
| 0.23 | 0.17 | 0.00 | 0.30 | 0.06 | 0.12 | 0.10 |

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Bensard, D. D., J. M. Brown, B. O. Anderson, A. Banerjee, P. F. Shanley, M. A Grosso, G. J. Whitman and A. H. Harken. (1990) Induction of endogenous tissue antioxidant enzyme activity attenuates myocardial reperfusion injury. *J. Surg. Res.* 49(2): 126–131.

Berg, J., R, Allison and A Taylor. (1990) Endotoxin extends survival of adult mice in hypoxia. *Proc. Soc. Exp. Biol. Med.* 193:167–170.

Brown J. M. et al. (1989) Endotoxin pretreatment increases endogenous myocardial catalase activity and decreases ischemia-reperfusion injury of isolated rat hearts. *Proc. Natl. Acad. Sci.* 86:2516–2520.

Elliot, U.S. Pat. No 5,286,718.

Elliot, G. (1998) Monophosphoryl Lipid A Induces Delayed Preconditioning Against Cardiac Ischemia-Reperfusion Injury. *J. Mol. Cell Cardiol.* 30:3–17.

Maulik N., M. Watanabe, D. Engelman, R. M. Engelman, V. E. Kagan, E. Kisin, V. Tyurin, G. A. Cordis and D. K. Das. (1995) Myocardial adaptation to ischemia by oxidative stress inducted by endotoxin. *Am. J. Physiol.* 269:C907–C916.

Mizumura, T., K. Nithipatikom and G. J. Gross. (1995) Bimakalim, an ATP-sensitive potassium channel opener, mimics the effects of ischemic preconditioning to reduce infarct size, adenosine release, and neutrophil function in dogs. *Circulation* 92:1236–1245.

What is claimed is:

1. A method for ameliorating organ or tissue injury in an animal caused by an ischemic event, said method comprising administering to said animal an effective amount of a phosphoglycolipid having the following structure:

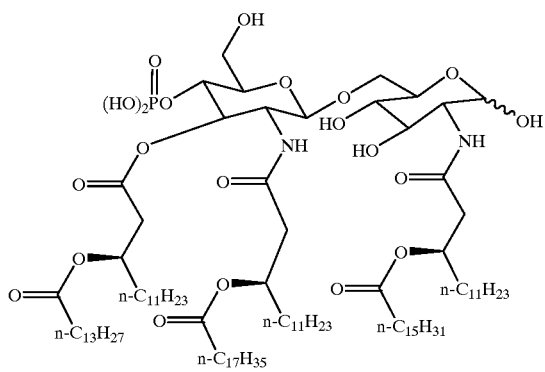

or a pharmaceutically acceptable salt thereof.

2. The method according to claim 1, wherein said phosphoglycolipid is administered to said animal from about 24 hours prior to the onset of ischemia up to the onset of ischemia.

3. The method according to claim 1, wherein said phosphoglycolipid is administered to said animal during ischemia.

4. The method according to claim 1, wherein said phosphoglycolipid is administered to said animal during reperfusion.

5. The method of claim 1, wherein said phosphoglycolipid is administered to said animal parenterally or orally.

6. The method of claim 1, wherein said phosphoglycolipid is administered to said animal intravenously.

7. The method of claim 1, wherein said phosphoglycolipid is administered to said animal as a bolus.

8. The method of claim 1, wherein said phosphoglycolipid is administered to said animal by infusion.

9. The method of claim 1, wherein said phosphoglycolipid is administered to said animal as a bolus followed by infusion.

10. The method of claim 1, wherein said phosphoglycolipid is administered to said animal intravenously as a bolus followed by infusion.

11. The method of claim 1, wherein said phosphoglycolipid is administered as a bolus to said animal in the amount of from about one to about 1000 micrograms per kilogram of the body weight of said animal.

12. The method of claim 1, wherein said phosphoglycolipid is administered as a bolus to said animal in the amount of from about 10 to about 300 micrograms per kilogram of the body weight of said animal.

13. The method of claim 1, wherein said phosphoglycolipid is administered as a bolus to said animal in the amount of from about 35 to about 100 micrograms per kilogram of the body weight of said animal.

14. The method of claim 1, wherein said ischemic event is an anticipated ischemic event.

15. The method of claim 2, wherein said anticipated ischemic event is associated with a condition selected from the group consisting of coronary artery bypass surgery, heart valve replacement, cardiac angioplasty, ventricular septal repairs, surgery with major vessel cross-clamping, plastic surgery, skin flap translocation, myoplasty, organ transplantation, tissue transplantation, aortic aneurysm repair, and bowel resection.

16. The method of claim 1, wherein said ischemic event is an unexpected ischemic event.

17. The method of claim 16, wherein said unexpected ischemic event is associated with a condition selected from the group consisting of myocardial infarction, stroke, drowning, bowel infarct, and traumatic amputation and reattachment.

* * * * *